United States Patent [19]

Shade et al.

[11] Patent Number: 4,809,554
[45] Date of Patent: Mar. 7, 1989

[54] ULTRASONIC INSECT DETECTOR

[75] Inventors: Richard E. Shade, Battleground; Eric S. Furgason, West Lafayette; Larry L. Murdock, Lafayette, all of Ind.

[73] Assignee: Purdue Research Foundation, West Lafayette, Ind.

[21] Appl. No.: 125,681

[22] Filed: Nov. 25, 1987

[51] Int. Cl.$^4$ ............................................. G01N 29/04
[52] U.S. Cl. ....................................... 73/587; 367/136
[58] Field of Search ................. 73/587, 591, 570, 584; 340/573; 367/136, 139; 381/120, 122

[56] References Cited

U.S. PATENT DOCUMENTS

| | | | |
|---|---|---|---|
| 4,410,967 | 10/1983 | Hendricks | 367/87 |
| 4,574,633 | 3/1986 | Ohnuki et al. | 73/587 |
| 4,629,834 | 12/1986 | Waggoner et al. | 381/122 |
| 4,671,114 | 6/1987 | Litzkow et al. | 73/587 |

FOREIGN PATENT DOCUMENTS

| | | |
|---|---|---|
| 2313833 | 10/1974 | Fed. Rep. of Germany . |
| 857865 | 8/1981 | U.S.S.R. . |
| 1407357 | 9/1975 | United Kingdom . |

OTHER PUBLICATIONS

Adams et al., "Aural Detection of Grain Infested Internally with Insects", *Science*, vol. 118, Aug. 7, 1953, pp. 163-164.

Adams et al., "Detection of Internal Insect Infestation in Grain by Sound Amplification", *Cereal Chemistry*, vol. 31, May 1954, pp. 271-276.

Pyrah, "New System Hears Insects Chewing", *Agricultural Research*, vol 33, No. 4, Apr. 1985, pp. 13-15.

Miller, "Femal Fruit Flies Desire Loud Males", *Agricultural Research*, vol. 34, No. 3, Mar. 1986, pp. 12-13.

Copy of Advertisement published in *Pest Control Operators Journal*, "Date Unknown".

Senft, "Microphones Monitor Plant's Water Needs", *Agricultural Research*, vol. 34, No. 3, Mar. 1986, p. 13.

*Primary Examiner*—Stewart J. Levy
*Assistant Examiner*—Louis M. Arana
*Attorney, Agent, or Firm*—Barnes & Thornburg

[57] ABSTRACT

An apparatus and method for detecting insects detects insects by detecting ultrasonic signals which are generated by mechanical disturbances in material on which insects are feeding caused by the insects feeding on the material.

36 Claims, 5 Drawing Sheets

ULTRASONIC INSECT DETECTOR

BACKGROUND AND SUMMARY OF THE INVENTION

This invention relates to electronic insect detection systems, and particularly to a system for detecting insects by detecting ultrasonic signals generated by the feeding of insects.

Hidden infestations of insects feeding and growing in wood and wood products, in seeds, and in other plant materials cause enormous economic loss in the United States each year. If, however, these infestations can be detected in their early stages and quantitatively assessed, potential damage can be predicted and timely pest management procedures such as fumigation or insecticide treatment can be implemented to prevent serious losses.

Discovery of infestations in their early stages by visual inspection is time consuming and ineffective because the number of insects involved is small, and the insects are tiny and usually hidden from view. Insect infestation begins with low levels of invasion of the product by the insect. Often an adult insect deposits eggs on the product from which immature stages of the insect (i.e., larvae) emerge and begin feeding and growing. Once the immature insects grow to maturity they begin reproducing, thereby increasing the severity of infestation and increasing the loss.

In studying insect biology and behavior, measuring plant damage by insects, or estimating insect numbers, the most appropriate variable to measure is usually the level of insect feeding activity.

Heretofore, insect detection systems which detect insect activity by detecting sound generated by insects have done so by detecting sound in the audio frequency range (20–20,000 Hz). In the audio frequency range, many sounds are detected which are not necessarily the result of insect feeding. These background noises, which mask the targeted feeding sounds, may be produced by non-feeding insect activity, or other environmental stresses on the plant tissue.

Previous insect detection devices have typically used transducers in the range of 200 Hz to 10,000 Hz. In order to isolate the detection system from background environmental noises, it was often necessary to construct a soundproof box to surround the transducer. The design of the soundproof box was often a difficult and time consuming task.

Applicants have found that technology commonly known as "Acoustic Emission" technology can be advantageously used in detecting insects. Heretofore, Acoustic Emission technology has primarily been used in the field of nondestructive testing of metal parts and assemblies. The component under test is subjected to a static stress which causes cracks in the metal part to grow (increase in length). As the crack grows, internal stresses around the crack tip are released which give rise to mechanical disturbances within the material. A transducer capable of converting mechanical waves to electrical signals is used to record the mechanical disturbances (acoustic emissions), thus providing some information related to the rate of crack growth.

Applicants have found that feeding insects produce ultrasonic signals which can be detected by the use of Acoustic Emission technology. As an insect feeds, it tears the fibrous tissue it is feeding on. The tearing of the fibrous tissue creates mechanical disturbances which propagate throughout the material on which the insect is feeding. These mechanical disturbances generate ultrasonic signals which can be detected by the use of Acoustic Emission technology.

An object of this invention is to provide an insect detection system which detects acoustic emissions emanated by feeding insects and which is relatively immune to background noise.

Another object of this invention is to provide an insect detection system which detects insects by detecting ultrasonic signals caused by insects feeding on material.

In accordance with the present invention, an apparatus for detecting insects includes means for detecting ultrasonic signals generated by the feeding of insects and generating first electrical signals therefrom. The invention further includes means for processing the first electrical signals to generate therefrom information about the feeding activity of the insects.

The insect detector of this invention uses an ultrasonic detecting device which is preferably sensitive to frequencies in the 40,000 Hz range. The use of the ultrasonic detecting device minimizes the effect of environmental background noises bcause the environment is relatively quiet in the frequency range above human hearing (20–20,000 Hz). Most human activities do not generate much acoustic energy at ultrasonic frequencies. Therefore, the sounds detected by the transducer are essentially those resulting from ultrasonic mechanical disturbances propagating through a material caused by the tearing of plant tissue during insect feeding activity. The ultrasonic mechanical disturbances are directly related to the action of the insect's mouthparts tearing the material during feeding. Each mechanical disturbance produced by an insect tearing the fibrous tissue, in other words taking a "bite" out of the material, will be termed a "feeding event."

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figures 1, 2:
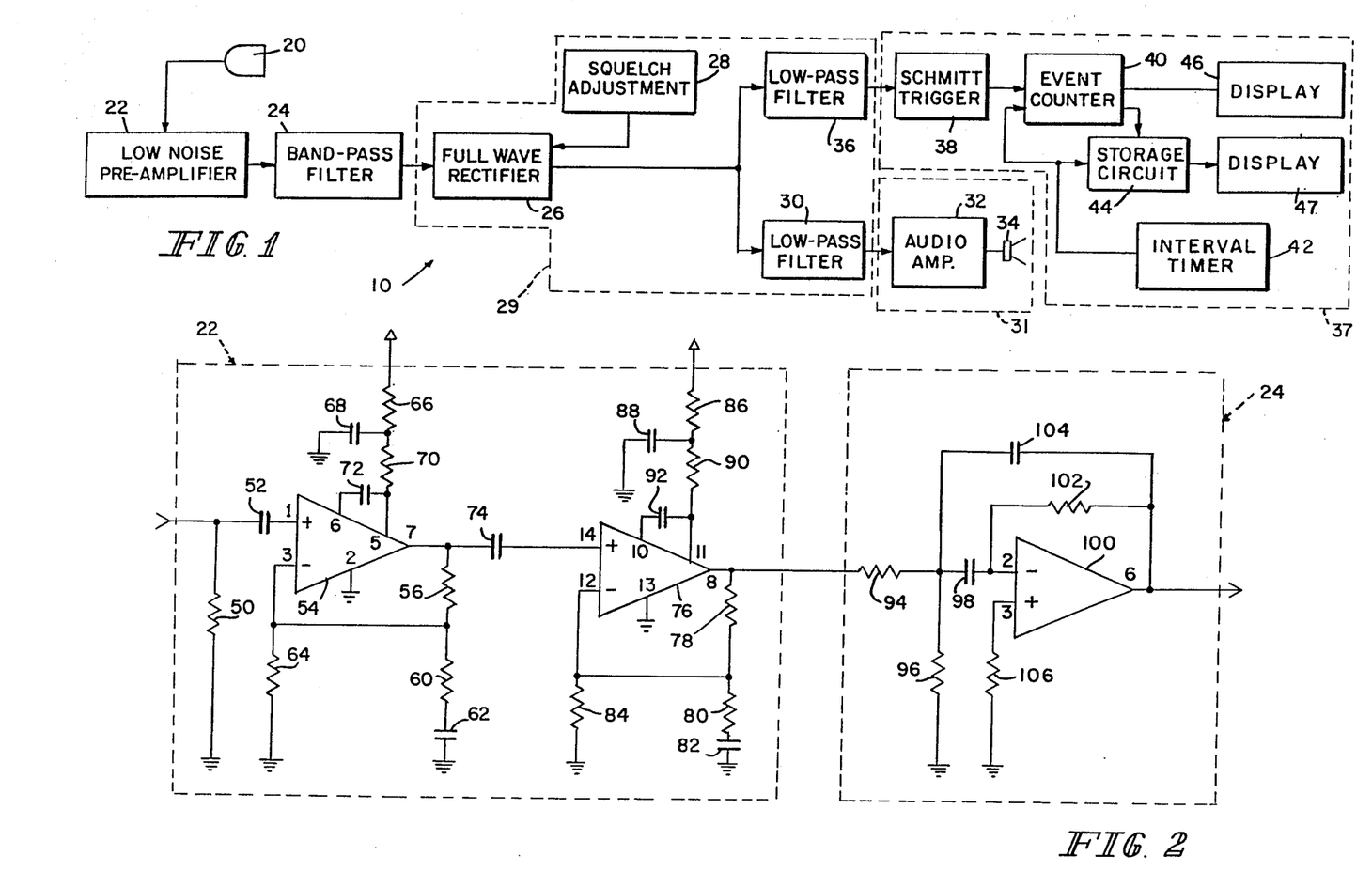
FIG. 1 is a block diagram of an ultrasonic insect detector according to this invention.
FIG. 2 is a schematic drawing of the preamplifier and band pass filter of FIG. 1.

Referring to FIG. 1, an ultrasonic insect detector 10 includes means 20 for detecting ultrasonic signals. Illustratively, means 20 is an ultrasonic transducer such as a piezolectric transducer which has a center frequency of 40 kHz. It should be understood that ultrasonic transducers having center frequencies other than 40 kHz can also be used. An output of ultrasonic transducer 20 is coupled to an input of a low-noise pre-amplifier 22. An output of pre-amplifier 22 is coupled to an input of a band-pass filter 24. An output of band-pass filter 24 is coupled to an input of a full wave rectifier 26. A squelch adjustment 28 is also coupled to an input of full wave rectifier 26. An output of full wave rectifier 26 is coupled to an input of a low-pass filter 30 and to an input of a low-pass filter 36. Full-wave rectifier 26, squelch adjustment 28, low-pass filter 30 and low-pass filter 36 comprise an envelope detector 29. An output of low-pass filter 30 is coupled to an input of an audio indicator circuit 31 and comprises an output of envelope detector 29 for audio indicator circuit 31. An output of low-pass filter 36 is coupled to an input of a digital indicator circuit 37 and comprises an output of envelope detector 29 for digital indicator circuit 37.

Audio indicator circuit 31 includes an audio amplifier 32 and an audio transducer 34, such as a loudspeaker. Digital indicator circuit 37 includes a Schmitt trigger 38, an event counter 40, a storage circuit 44, an interval timer 42 and visual displays 46, 47. The output of low-pass filter 30 is coupled to an input of an audio amplifier 32. The output of audio amplifier 32 is coupled to an input of an audio transducer 34.

The output of low-pass filter 36 is coupled to an input of Schmitt trigger 38. An output of Schmitt trigger 38 is coupled to an input of event counter 40. An output of event counter 40 is coupled to an input of display 46 and to an input of storage circuit 44. An output of storage circuit 44 is coupled to an input of display 47. Interval timer 42 is coupled to an input of event counter 40 and to an input of storage circuit 44.

In operation, ultrasonic transducer 20 detects the ultrasonic signals which are generated by the mechanical disturbances propagating through a material caused by insects feeding on the material. Ultrasonic transducer 20 converts the detected ultrasonic signals to electrical signals which have the same frequency as the detected ultrasonic signals. The detected ultrasonic signals have very low amplitudes and consequently the electrical signals produced by ultrasonic transducer 20 also have very low amplitudes. Pre-amplifier 22 amplifies these electrical signals and is designed to introduce as little unwanted electrical noise as possible, although it inevitably introduces some. The amplified electrical signals are band-pass filtered by band-pass filter 24.

Band-pass filter 24 is designed to permit only the electrical signals which originated from transducer 20 to pass and to filter out all other electrical signals. Since ultrasonic transducer 20 is sensitive to only a narrow range of frequencies centered about its center frequencies, any electrical signals at the input of band-pass filter 24 which have frequencies outside this narrow range are unwanted electrical signals such as electrical noise which may have been introduced by pre-amplifier 22. Due to the very low amplitudes of the electrical signals produced by ultrasonic transducer 20, the noise introduced by pre-amplifier 22 may be significant. Band-pass filter 24 eliminates the unwanted electrical signals, such as the noise introduced by pre-amplifier 22, by passing only electrical signals having frequencies falling within a narrow range centered about its center frequency. Illustratively, band-pass filter 24 is a narrow band band-pass filter having a center frequency the same as the center frequency of ultrasonic transducer 20 and a band-pass which is the same as the range of frequencies to which ultrasonic transducer 20 is sensitive. The filtered output signals of band-pass filter 24 will have sufficient amplitude to be relatively immune to contamination from electrical noise since their amplitudes will be significantly higher than any electrical noise introduced by the remainder of ultrasonic insect detector 10.

The filtered output signals from band-pass filter 24 are then envelope detected by envelope detector 29. Since the objective is to detect feeding events, it is only necessary to determine whether or not a burst of acoustic energy is present at any instant in time. This is accomplished by processing the envelope or broad outline of the filtered signals from band-pass filter 24.

The first step in determining the envelope or outline of the filtered signals from band-pass filter 24 is to pass these signals through full wave rectifier 26. The electrical signals produced by ultrasonic transducer 20 are oscillatory in nature which produces oscillating signals at the output of band-pass filter 24 which swing about zero. Thus, the average value of these signals over time is zero. Full wave rectifier 26 leaves the positive portion of these signals unchanged but inverts the negative portion of the signal and the resulting output signal (for an individual feeding event) of full wave rectifier 26 will no longer have an average value over time of zero. In fact, the average value of the rectified signal over time for an individual feeding event is now proportional to the size or amplitude of the signal.

Low-pass filters 30, 36 average the rectified signal over time to provide a running average of the size of the rectified signals for audio indicator circuit 31 and digital indicator circuit 37, respectively. The time over which this running average is computed is determined by the bandwidth of the filters and is the reciprocal of the filter bandwidth. Therefore, a small bandwidth means averaging over a longer period of time. Since low-pass filters 30 and 36 are low-pass filters, their bandwidths are measured from 0 Hz to their cut-off frequencies. Illustratively, low-pass filter 30 has a cut-off frequency of 5 kHz and low-pass filter 36 has a cut-off frequency of 20 Hz. Squelch adjustment 28 permits ultrasonic insect detector 10 to distinguish between large and small signals by providing a threshold level to rectifier 26. Rectifier 26 passes only those signals which have levels greater than the threshold level. Squelch adjustment 28 is illustratively adjustable by an operator or user of ultrasonic insect detector 10.

Audio indicator circuit 31 produces an audio indication of the activity of the insect, i.e., the rate at which the acoustic events (feeding events) occur. The output of low-pass filter 30, which comprises the envelope of the ultrasonic signal detected by transducer 20 processed to produce a signal in the audible range, is amplified by amplifier 32 and output over speaker 34. The sound heard from speaker 34 is not the sound of the ultrasonic signal detected by ultrasonic transducer 20. The ultrasonic signal detected by ultrasonic transducer 20 is well outside the range of human hearing. To produce signals audible to the human ear, the envelope of the ultrasonic signal detected by transducer 20 is produced as described so that the sounds emanating from speaker 34 are produced by the envelope of the ultrasonic signals detected by transducer 20. Thus, the user of ultrasonic insect detector 10 hears a sound corresponding to each major acoustic event. Further, although all the details of the ultrasonic signals which result from the tearing of plant tissue are not present in the envelope signals produced at the output of low-pass filter 30, the cut-off frequency of low-pass filter 30, illustratively 5 kHz, is selected so that some details of the detected feeding activity are present in the envelope signals. This permits the operator of insect detector 10 to evaluate somewhat the nature of the detected feeding activity as well as the level or amount of feeding activity present.

Digital indicator circuit 37 provides a digital output indicative of the detected feeding activity of the insects. Illustratively, this is a visual display which displays a number which represents the number of feeding events detected. It could also be a binary signal suitable for input to a computer for further processing.

The envelope of the ultrasonic signal detected by transducer 20 which is produced at the output of low-pass filter 36 is processed by Schmitt trigger 38 to produce a binary signal suitable for input to a computer or to event counter 40. To produce a digital output suitable for input to a computer or as an input to the event counter 40, a decision must be made at each instant of time whether an acoustic event (feeding event) has taken place. Schmitt trigger 38 performs that decision making process by comparing the envelope of the signal generated at the output of low-pass filter 36 to a predetermined threshold and producing a binary signal based upon the comparison. If the envelope signal exceeds the threshold, Schmitt trigger 38 produces a signal corresponding to a logical one. If not, Schmitt trigger 38 produces a signal corresponding to a logical zero. The output of Schmitt trigger 38 can be coupled to a computer which can analyze the insect feeding activity.

Displays 46, 47 display numbers which are the current number of feeding events detected, as accumulated by event counter 40, and the number of feeding events detected during a just elapsed measuring period or interval, respectively. Event counter 40 counts the feeding events detected by ultrasonic insect detector 10 by counting each binary one produced by Schmitt trigger 38. Event counter 40 drives visual display 46 which displays the current number of feeding events detected by ultrasonic insect detector 10.

The measuring period is determined by interval timer 42. At the end of the measuring period, the total in event counter 40 is passed to storage circuit 44. In turn, storage circuit 44 drives visual display 47 which displays the number of feeding events detected by ultrasonic insect detector 10 during the just elapsed measuring period.

FIG. 2 is a schematic of a circuit for preamplifier 22 and band-pass filter 24 of FIG. 1. Preamplifier 22 includes operational amplifiers 54, 76, and their associated components, a 3.92k resistor 50, a 0.33 uF capacitor 52, a 18k resistor 56, a 220 ohm resistor 60, a 0.033 uF capacitor 62, a 1.0k resistor 64, a 22k resistor 66, a 10 uF capacitor 68, a 75k resistor 70, a 30 pF capacitor 72, a 0.1 uF capacitor 74, a 22k resistor 78, a 240 ohm resistor 80, a 0.47 uF capacitor 82, a 1.0k resistor 84, a 22k resistor 86, a 10 uF capacitor 88, a 62k resistor 90, and a 30 pF capacitor 92. Band-pass filter 24 includes operational amplifier 100 and its associated components, a 49.9k resistor 94, a 1.00k resistor 96, a 390 pF capacitor 98, a 100k resistor 102, a 390 pF capacitor 104, and a 100k resistor 106. A LM381 dual operational amplifier manufactured by National Semiconductor Corporation, 2900 Semiconductor Drive, Santa Clara, Calif. 95051, illustratively comprises operational amplifiers 54, 76 and operational amplifier 100 is illustratively a LM318J-8 operational amplifier also manufactured by National Semiconductor.

The output of ultrasonic transducer 20 (FIG. 1) is coupled through resistor 50 to ground and through capacitor 52 to a non-inverting (+) input (pin 1) of operational amplifier 54. An output of operational amplifier 54 (pin 7) is coupled to a first terminal of resistor 56. A second terminal of resistor 56 is coupled to ground through a series string of resistor 60 and capacitor 62. The second terminal of resistor 56 is also coupled to ground through resistor 64 and to an inverting (−) input (pin 3) of operational amplifier 54.

A first terminal of resistor 66 is coupled to a source of V+ (not shown), illustratively +15 VDC. A second terminal of resistor 66 is coupled through capacitor 68 to ground and to a first external compensation input (pin 5) of operational amplifier 54 through resistor 70. Capacitor 72 is coupled between the first external compensation input (pin 5) and a second external compensation input (pin 6) of operational amplifier 54. Pin 2 of operational amplifier 54 is coupled to ground.

The output (pin 7) of operational amplifier 54 is coupled through capacitor 74 to the (+) input (pin 14) of operational amplifier 76. An output (pin 8) of amplifier 76 is coupled to a first terminal of resistor 78. A second terminal of resistor 78 is coupled to ground through a series combination of resistor 80 and capacitor 82. The second terminal of resistor 78 is also coupled to ground through resistor 84 and to a (−) input (pin 12) of operational amplifier 76.

A first terminal of resistor 86 is coupled to V+. A second terminal of resistor 86 is coupled to ground through capacitor 88 and through resistor 90 to a first external compensation input (pin 11) of operational amplifier 76. A second external compensation input (pin 10) of operational amplifier 76 is coupled through capacitor 92 to the first external compensation input (pin 11) of operational amplifier 76. Pin 13 of operational amplifier 76 is coupled to ground.

The output (pin 8) of preamplifier 22 is coupled to the input of band-pass filter 24. Specifically, the output (pin 8) of operational amplifier 76 is coupled to a first terminal of resistor 94 of band-pass filter 24. A second terminal of resistor 94 is coupled through capacitor 98 to a (−) input (pin 2) of operational amplifier 100, through capacitor 104 to an output (pin 6) of operational amplifier 100 and through resistor 96 to ground. A (+) input (pin 3) of operational amplifier 100 is coupled through resistor 106 to ground. The output (pin 6) of operational amplifier 100 is coupled through resistor 102 to the (−) input (pin 2) of operational amplifier 100. The output (pin 6) of operational amplifier 100 comprises the output of band-pass filter 24.

Figure 3:
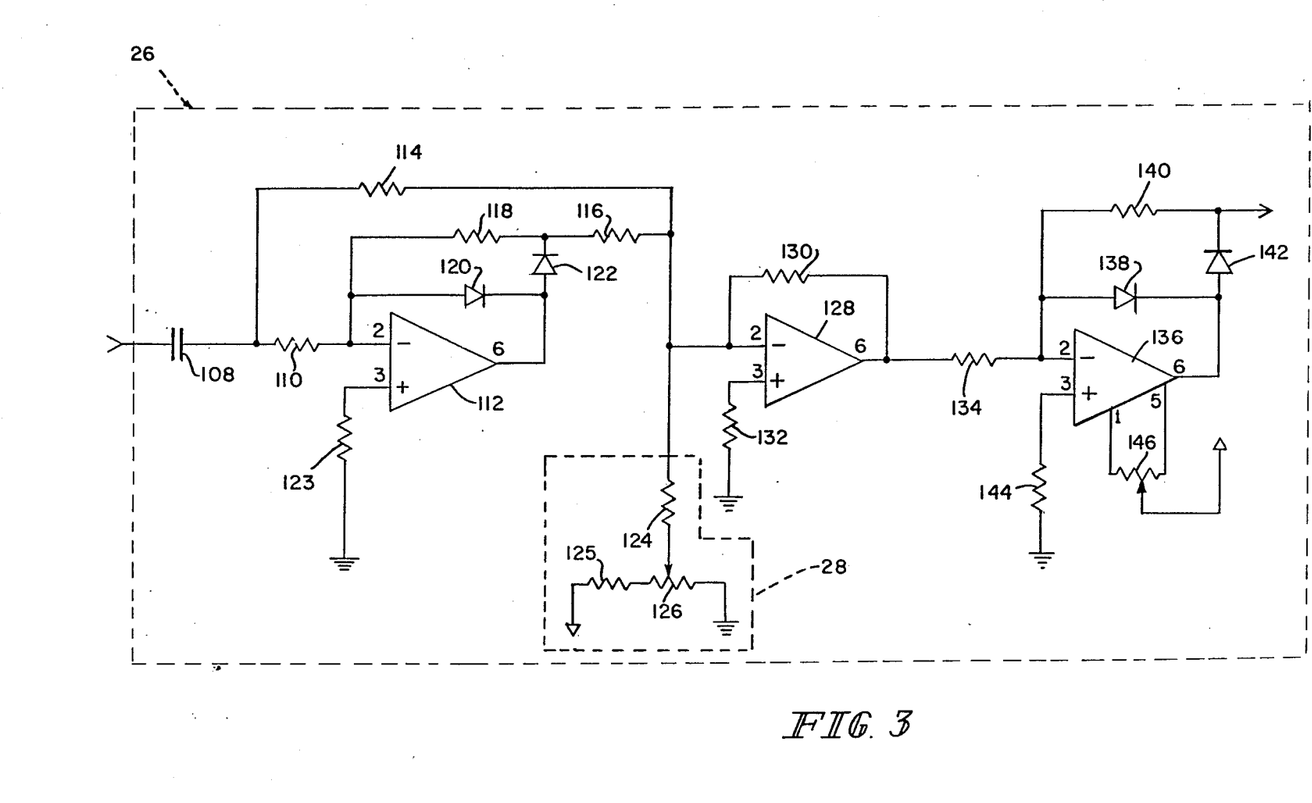
FIG. 3 is a schematic diagram of the full wave rectifier and squelch adjustment of FIG. 1.

FIG. 3 is a schematic of a circuit for the full wave rectifier 26 and squelch adjustment 28 of FIG. 1. Full wave rectifier 26 includes a 0.033 uF capacitor 108, a 2.00k resistor 110, an operational amplifier 112, a 20.0k resistor 114, a 10.0k resistor 116, a 2.00k resistor 118, diodes 120, 122, a 1.0k resistor 123, an operational amplifier 128, a 20.0k resistor 130, a 3.3k resistor 132, a 2.0k resistor 134, an operational amplifier 136, diodes 138, 142, a 3.9k resistor 140, a 1.3k resistor 144, and a 100k potentiometer 146. Illustratively, operational amplifiers 112, 128, 136 are LM318J-8 operational amplifiers manufactured by National Semiconductor. Squelch adjustment 28 comprises a 100k resistor 124, a 10k resistor 125 and a 1k potentiometer 126.

The output of band-pass filter 24 (pin 6 of operational amplifier 100) is coupled through capacitor 108 of full wave rectifier 26 to a first terminal of resistor 110 and to a first terminal of feedthrough resistor 114. A second terminal of resistor 110 is coupled to a (−) input (pin 2) of operational amplifier 112. The (−) input of operational amplifier 112 is also coupled to the anode of diode 120 and through resistor 118 to a junction of the cathode of diode 122 and a first terminal of resistor 116. A (+) input (pin 3) of operational amplifier 112 is coupled through resistor 123 to ground. An output (pin 6) of operational amplifier 112 is coupled to the anode of diode 122 and to the cathode of diode 120.

A second terminal of resistor 116 is coupled to a (−) input (pin 2) of operational amplifier 128 as is a second terminal of resistor 114. The (−) input of operational amplifier 128 is also coupled to a first terminal of resistor 124 of squelch adjustment 28. A second terminal of resistor 124 is coupled to the center tap of potentiometer 126. One side of potentiometer 126 is coupled to ground and the other side of potentiometer 126 is coupled to a source of −15 VDC (not shown) through a 10k resistor 125. A (+) input (pin 3) of operational amplifier 128 is coupled to ground. An output (pin 6) of operational amplifier 128 is coupled through resistor 130 to the (−) input of operational amplifier 128 and through resistor 134 to a (−) input (pin 2) of operational amplifier 136. The (−) input of operational amplifier 136 is also coupled to the anode of diode 138 and through resistor 140 to the cathode of diode 142. An output (pin 6) of operational amplifier 136 is coupled to the anode of diode 142 and to the cathode of diode 138. A first balance compensation terminal (pin 1) of operational amplifier 136 is coupled to one side of potentiometer 146 and a second balance compensation terminal (pin 5) of operational amplifier 136 is coupled to the other side of potentiometer 146. The center tap of potentiometer 146 is coupled to +V.

Full wave rectifier 26 and squelch adjustment 28 operate as follows. Operational amplifiers 112 and 136 are configured as half-wave rectifiers and operational amplifier 128 is configured as a summing amplifier. The filtered signal provided by bandpass filter 24 is first half-wave rectified by operational amplifier 112 and fed through resistor 116 to the (−) input of operational amplifier 128. The filtered signal provided by bandpass filter 24 is also fed through feedthrough resistor 114 to the (−) input of operational amplifier 128. The (−) input of operational amplifier 128 thus comprises a summing junction. The half-wave rectified signal from operational amplifier 112 and the filtered signal from bandpass filter 24 are summed at the (−) input of operational amplifier 128 and the resulting signal produced at the output of operational amplifier 128 is a full-wave rectified signal of the filtered signal provided by bandpass filter 24.

Squelch adjustment 28, as discussed, permits ultrasonic insect detector 10 to discriminate between high and low signals. It provides a negative DC offset to the (−) input of operational amplifier 128. If the signals at the (−) input of operational amplifier 128 have a magnitude less than the magnitude of the DC offset, operational amplifier 128 produces a zero level output. If the signals at the (−) input of operational amplifier 128 have a magnitude greater than the DC offset, operational amplifier produces an output signal which is the full-wave rectified signal of the filtered signal provided by bandpass filter 24.

The full-wave rectified signal produced at the output of operational amplifier 128 is then half-wave rectified by operational amplifier 136 to eliminate any negative DC offset introduced by squelch adjustment 28. The junction of the cathode of diode 142 and the second terminal of resistor 140 comprise the output of full wave rectifier 26 at which the full wave rectified signal of band-pass filter 24 is provided.

Figure 4:
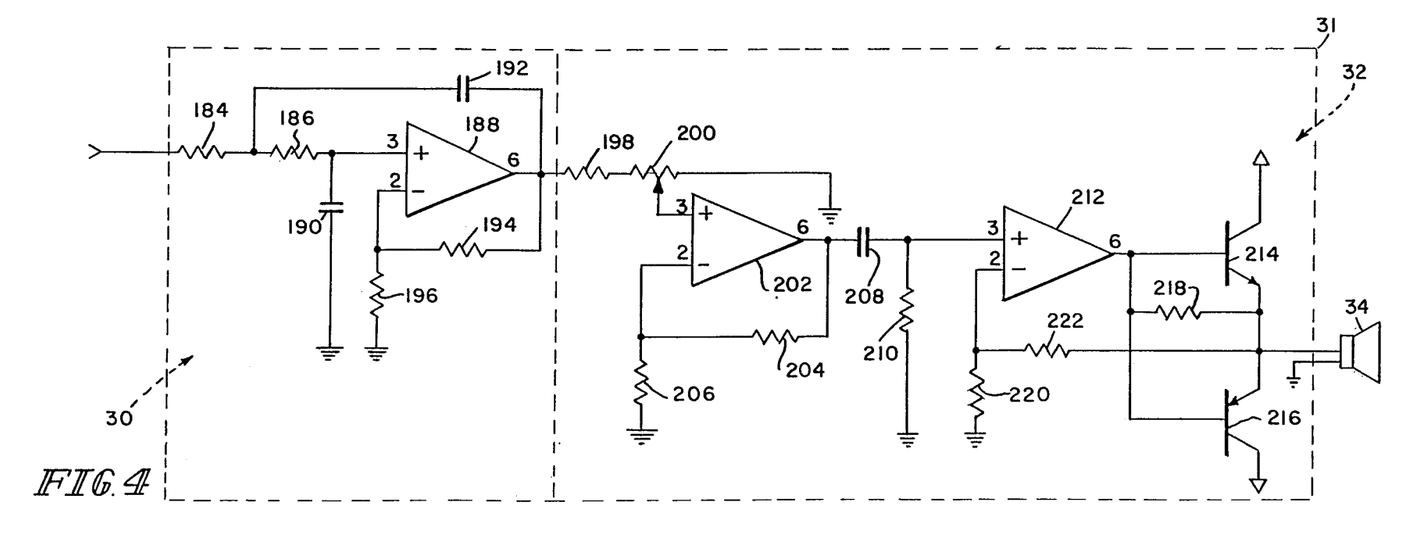
FIG. 4 is a schematic diagram of the audio indicator circuit of FIG. 1.

FIG. 4 is a schematic of a circuit for low-pass filter 30 of envelope detector 29 and audio amplifier 32 of audio circuit 31 of FIG. 1. Low-pass filter 30 includes a 33k resistor 184, a 33k resistor 186, an operational amplifier 188, a 1 nF capacitor 190, a 1 nF capacitor 192, a 5.6k resistor 194, and a 10k resistor 196. Audio amplifier 32 includes a 1.0k resistor 198, a 1.0k potentiometer 200, an operational amplifier 202, a 100k resistor 204, a 11k resistor 206, a 0.1 uF capacitor 208, a 15k resistor 210, an operational amplifier 212, a NPN transistor 214, a PNP transistor 216, a 51 ohm resistor 218, a 11k resistor 220, and a 100k resistor 222. Illustratively, operational amplifiers 188, 202 and 212 are LM 741CJ operational amplifiers manufactured by National Semiconductor.

The output of full wave rectifier 26 (the junction between the cathode of diode 142 and the second terminal of resistor 140) is coupled through resistor 184 to one terminal of resistor 186 and to one terminal of capacitor 192. A second terminal of resistor 186 is coupled to a (+) input (pin 3) of operational amplifier 188 and through capacitor 190 to ground. A (−) input (pin 2) of operational amplifier 188 is coupled through resistor 194 to an output (pin 6) of operational amplifier 188 and through resistor 196 to ground. The output of operational amplifier 188 is also coupled to a second terminal of capacitor 192 and also provides the output of low-pass filter 30.

The output of low-pass filter 30 is coupled through resistor 198 of audio amplifier 32 to one side of potentiometer 200. The other side of potentiometer 200 is coupled to ground. The center tap of potentiometer 200 is coupled to a (+) input (pin 3) of operational amplifier 202. A (−) input (pin 2) of operational amplifier 202 is coupled through resistor 204 to an output (pin 6) of operational amplifier 202 and through resistor 206 to ground. The output of operational amplifier 202 is coupled through capacitor 208 to a (+) input (pin 3) of operational amplifier 212. The (+) input of operational amplifier 212 is also coupled through resistor 210 to ground. A (−) input (pin 2) of operational amplifier 212 is coupled through resistor 220 to ground and through resistor 222 to the emitters of transistors 214, 216. An output (pin 6) of operational amplifier 212 is coupled to the bases of transistor 214, 216 and through resistor 218 to the emitters of transistors 214, 216. The collector of transistor 214 is coupled to V+ and the collector of transistor 216 is coupled to a source of V− (not shown), illustratively a source of −15 VDC. The emitters of transistors 214, 216 provide the output of audio amplifier 32 and are coupled to speaker 34.

Figure 5:
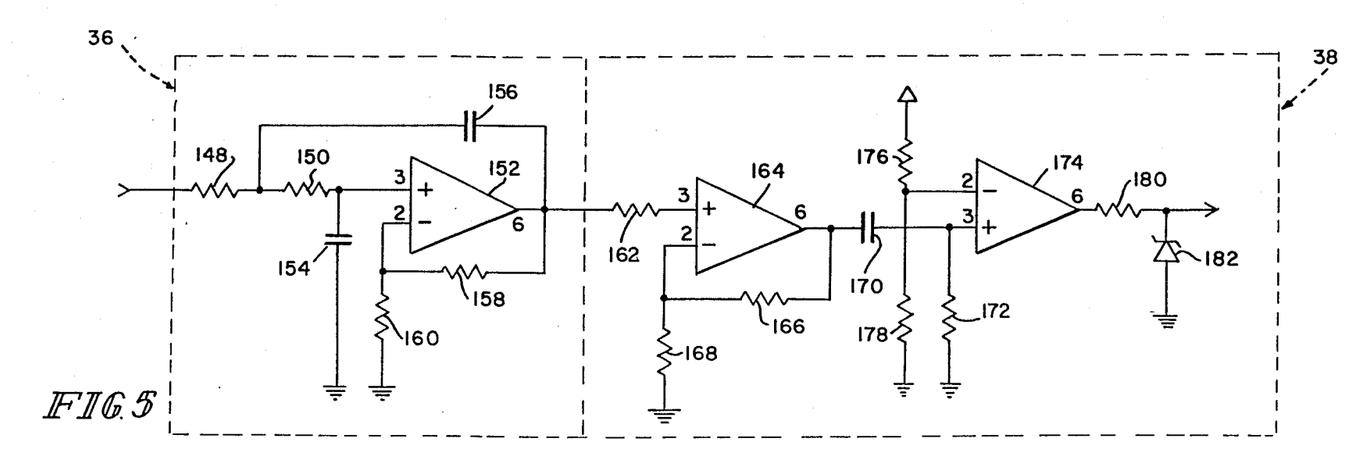
FIG. 5 is a schematic diagram of the low pass filter and Schmitt trigger of FIG. 1.

FIG. 5 is a schematic diagram of a circuit for low-pass filter 36 and a circuit for Schmitt trigger 38 of FIG. 1. Low-pass filter 36 includes a 75k resistor 148, a 75k resistor 150, an operational amplifier 152, a 100 nF capacitor 154, a 100 nF capacitor 156, a 160k resistor 158, and a 270k resistor 160. Schmitt trigger 38 includes a 2.0k resistor 162, an operational amplifier 164, a 220k resistor 166, a 2.2k resistor 168, a 10 uF capacitor 170, a 3.3k resistor 172, an operational amplifier 174, a 10M resistor 176, a 3.3k resistor 178, a 2.2k resistor 180, and 4.7 V zener diode 182. Illustratively, operational amplifiers 152, 164, 174 are LM 741 operational amplifiers manufactured by National Semiconductor.

The output of full wave rectifier 26 (the junction of the cathode of diode 142 and the second terminal of resistor 140) is coupled through resistor 148 to a first terminal of resistor 150 and to a first terminal of capacitor 156. A second terminal of resistor 150 is coupled to a (+) input (pin 3) of operational amplifier 152 and through capacitor 154 to ground. A (−) input (pin 2) of operational amplifier 152 is coupled through resistor 160 to ground and through resistor 158 to an output (pin 6) of operational amplifier 152. The output of operational amplifier 152 is also coupled to the second terminal of capacitor 156 and also provides the output of low-pass filter 136.

The output of low-pass filter 36 (pin 6 of operational amplifier 152) is coupled through resistor 162 to a (+) input (pin 3) of operational amplifier 164 of Schmitt trigger 38. A (−) input (pin 2) of operational amplifier 164 is coupled through resistor 168 to ground and through resistor 166 to an output (pin 6) of operational amplifier 164. The output of operational amplifier 164 is coupled through capacitor 170 to a (+) input (pin 3) of operational amplifier 174. The (+) input of operational amplifier 174 is also coupled through resistor 172 to ground. A negative input (pin 2) of operational amplifier 174 is coupled through resistor 176 to V+ and through resistor 178 to ground. An output (pin 6) of operational amplifier 174 is coupled through resistor 180 to the cathode of zener diode 182. The anode of zener diode 182 is coupled to ground. The junction of the cathode of zener diode 182 and resistor 180 comprises the output of Schmitt trigger 38 at which a "count" signal, i.e., a binary one as discussed previously, is generated when ultrasonic insect detector 10 detects a feeding event.

Figure 6:
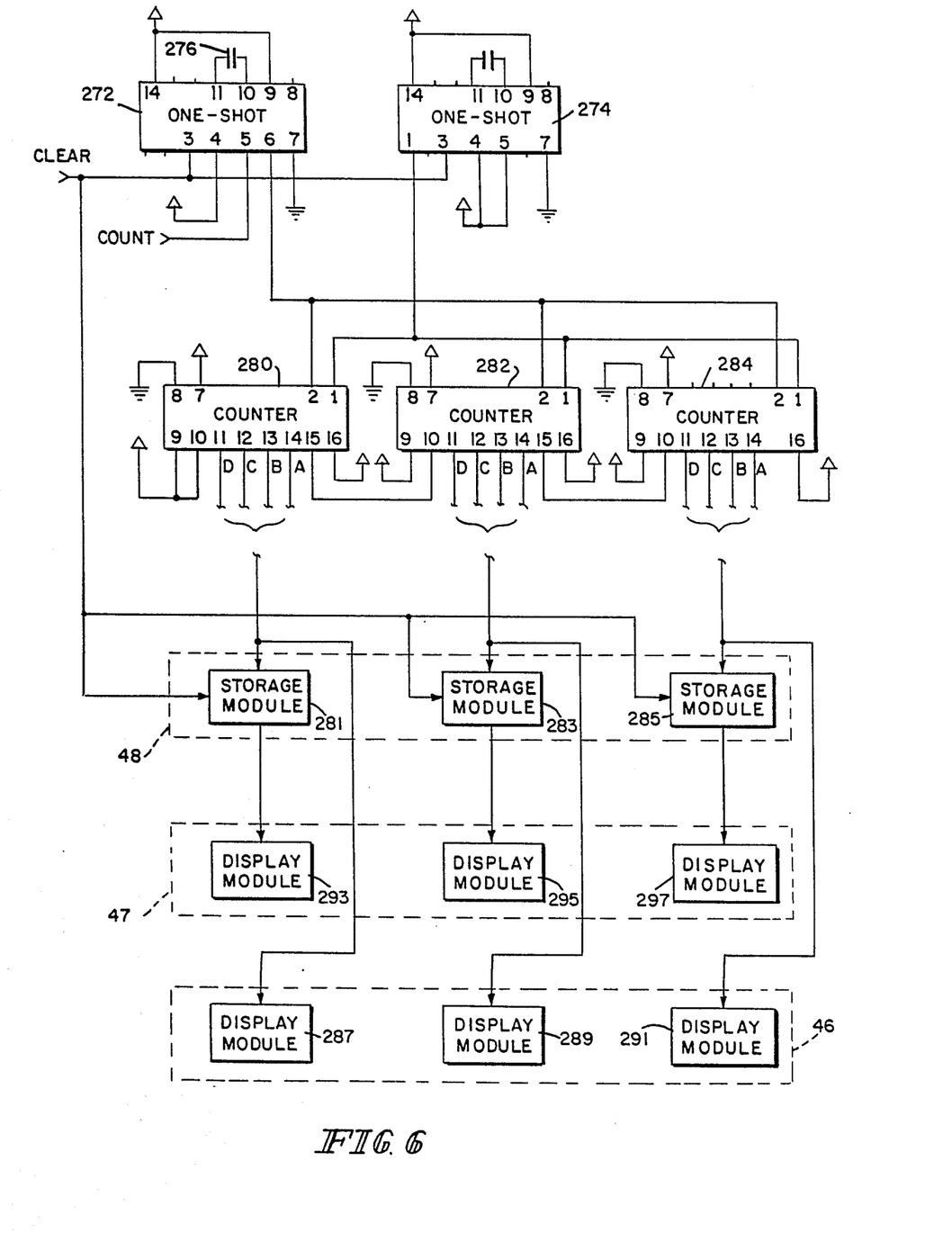
FIG. 6 is a schematic diagram of the event counter of FIG. 1.

FIG. 6 is a schematic diagram of a circuit for event counter 40 of FIG. 1 coupled to storage circuit 44 and visual displays 46, 47. A "clear" signal, produced by interval timer 42 as discussed in more detail later, is provided to negative-transition inputs (pin 3) of one-shots 272, 274. The output of Schmitt trigger 38, which produces a count signal each time a feeding event is detected as has been discussed, is coupled to a positive-transition input (pin 5) of one-shot 272. Illustratively, one-shots 272, 274 are SN 74121 monostable multivibrators manufactured by Texas Instruments, Inc., P.O. Box 5012, Dallas, Tex. 75222. A second negative-transition input (pin 4) of one-shot 272 is coupled to a source of +5 VDC as are the internal timing resistor (pin 9) and a power supply terminal (pin 14) of one-shot 272. A ground terminal (pin 7) of one-shot 272 is coupled to ground. A 33 pF external timing capacitor 276 is coupled between a first timing input (pin 10) and a second timing input (pin 11) of one-shot 272. The Q output (pin 6) of one-shot 272 is coupled to clock inputs (pin 2) of counters 280, 282 and 284. One-shot 272 comprises a glitch suppressor which suppresses glitches on the count signal produced by Schmitt trigger 38 and produces a 45 ns. positive count pulse at its Q output (pin 6) every time Schmitt trigger 38 produces a count signal.

One-shot 274 comprises a glitch suppressor which suppresses glitches or spikes on the clear signal and also inverts the clear signal by producing a 45 ns. negative going clear signal every time a clear signal is produced by interval timer 42. A second negative-transition input (pin 4) and a positive-transition input (pin 5) of one-shot 274 are coupled to the source of +5 VCD (not shown) as are the internal timing resistor (pin 9) and a power supply terminal (pin 14) of one-shot 274. A 33 pF external timing capacitor 278 is coupled between a first timing input (pin 10) and a second timing input (pin 11) of one-shot 274. A ground terminal (pin 7) of one-shot 274 is coupled to ground. The Q-not output (pin 1) of one-shot 274 is coupled to clear inputs (pin 1) of counters 280, 282 and 284.

Counters 280, 282 and 284 count the feeding events detected by ultrasonic insect detector 10 by counting the count pulses generated by one-shot 272. Counters 280, 282 and 284 are illustratively SN 74160 decade, direct clear counters manufactured by Texas Instruments. The count accumulated in each of counters 280, 282 and 284 comprises one digit of a three digit counter. Thus, event counter 40 is a three digit counter and can count up to 999 feeding events. Counter 280 contains the least significant digit, counter 282 contains the second least significant digit, and counter 284 contains the most significant digit of the three digit counter which is event counter 40. A P enable input (pin 7), a load input (pin 9), and a power supply terminal (pin 16) of each of counters 280, 282 and 284 are coupled to the source of a +5 VDC (not shown) and pin 8 of each counter 280, 282 and 284 is coupled to ground. A T enable input (pin 10) of counter 280 is also coupled to the source of +5 VDC (not shown). A ripple carry output (pin 15) of counter 280 is coupled to a T enable input (pin 10) of counter 282. A ripple carry output (pin 15) of counter 282 is coupled to a T enable input (pin 10) of counter 284. Data outputs (pins 11, 12, 13 and 14) of counters 280, 282, 284 are coupled to data inputs of storage modules 281, 283, 285, respectively, of data storage circuit 44 and to data inputs of display modules 287, 289, 291, respectively, of visual display 46. Data outputs of storage modules 281, 283, 285 are coupled to data inputs of display modules 293, 295, 297 of visual display 47. In FIG. 6, the letters A, B, C and D are used to indicate the least significant bit to the most significant bit, respectively, of the particular outputs of counters 280, 282, 284.

As discussed, counters 280, 282, 284 accumulate the feeding events detected by ultrasonic insect detector 10. The accumulated count in each counter 280, 282, 284 is continuously output to display modules 287, 289, 291, respectively, of visual display 46 to display the current count of detected feeding events. Further, after the elapse of the measuring period determined by interval timer 42, the accumulated count in each counter 280, 282, 284 is latched into storage modules 293, 295, 297, respectively, by the clear signal generated by interval timer 42. This clear signal also resets counters 280, 282, 284 to zero. Thus, after the elapse of the measuring period, visual display 47 will display the number of feeding events detected by ultrasonic insect detector 10 in the just elapsed measuring period and visual display 46 will begin displaying the number of detected feeding events currently being accumulated by ultrasonic insect detector 10. Illustratively, storage modules 281, 283, 285 are SN 7475 latches manufactured by Texas Instruments and display modules 287, 289, 291, 293, 295, 297 each comprise a BCD-TO-SEVEN SEGMENT DECODER/DRIVER coupled to a 7-SEGMENT display. Illustratively, the BCD-TO-SEVEN SEGMENT DECODER/DRIVERS are SN 7448 integrated circuits manufactured by Texas Instruments and the 7-SEGMENT displays are 5082-7740 displays manufactured by Hewlett-Packard, 620 Page Mill Road, Palo Alto, Calif. 94304.

Figure 7:
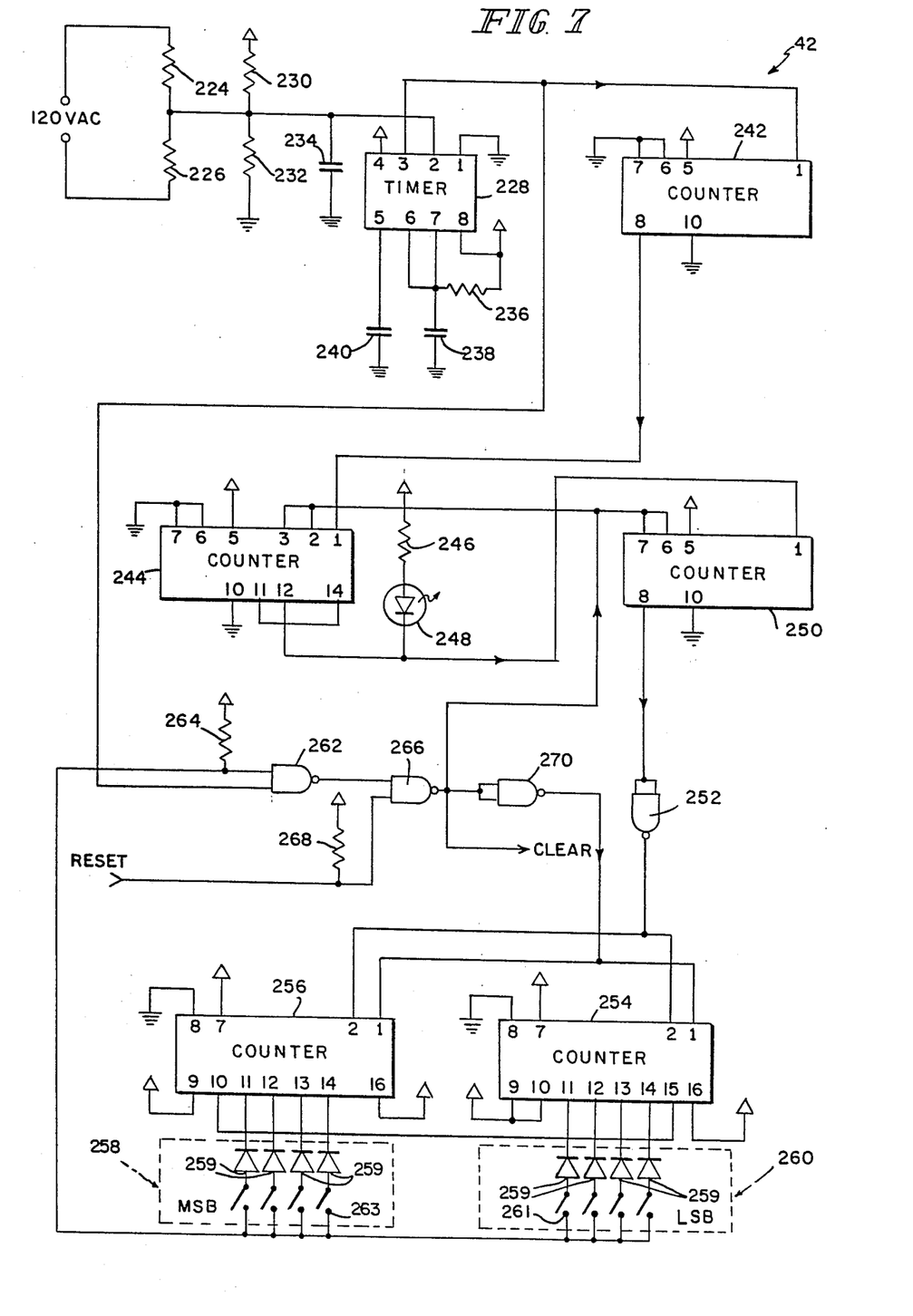
FIG. 7 is a schematic diagram of the interval timer of FIG. 1.

FIG. 7 is a schematic of a circuit for interval timer 42 of FIG. 1. A first terminal of a 10M resistor 224 is coupled to one side of a source of 60 cycle, 120 volts alternating current (VAC), such as house current, and a first terminal of a 10M resistor 226 is coupled to the other side of the source of 60 cycle, 120 VAC. Second terminals of resistors 224 and 226 are coupled together and to a trigger input (pin 2) of a timer 228. The trigger input of timer 228 is also coupled through a 1M resistor 230 to the source of +5 VDC (not shown), through a 1M resistor 232 to ground and through a 0.01 uF capacitor 234 to ground. A power supply terminal (pin 8) of timer 228 is coupled to the source of +5 VDC as is a reset input (pin 4) of timer 228. A ground terminal (pin 1) of timer 228 is coupled to ground. Discharge and threshold terminals (pins 7 and 6, respectively) of timer 228 are coupled to the source of +5 VDC through a 150k resistor 236 and to ground through a 0.05 uF capacitor 238. A control voltage terminal (pin 5) of timer 228 is coupled to ground through a 0.1 uF capacitor 240. Illustratively, timer 228 is a LM 555 manufactured by National Semiconductor, configured as a monostable multivibrator, and produces a 8.25 ms pulse each time it is triggered by a low-to-high transition at its trigger input (pin 2). Timer 228 thus converts the 60 cycle, 120 VAC signal to a pulse train having a frequency of 60 Hz.

The 60 Hz pulse train produced by timer 228 is next divided by six by a divide-by-six counter 242 which produces a 10 Hz square wave at its $Q_D$ output (pin 8). Illustratively, counter 242 is a SN 7492 counter manufactured by Texas Instruments and configured as a divide-by-six counter. An output of timer 228 (pin 3) is coupled to a count input (pin 1) of counter 242. A power terminal (pin 5) of counter 242 is coupled to the source of +5 VDC (not shown). A ground terminal (pin 10) of counter 242 is coupled to ground as are reset inputs $R_{0(1)}$ and $R_{0(2)}$ (pins 6 and 7, respectively) of counter 242.

A divide-by-ten counter 244 divides the 10 Hz square wave produced by counter 242 by ten to produce at its $Q_A$ output (pin 12) a 1 Hz square wave. Illustratively, counter 244 is a SN 7490 counter manufactured by Texas Instruments configured as a divide-by-ten counter. The ouput (pin 8) of counter 242 is coupled to a count input (pin 1) of counter 244. Reset inputs $R_{0(1)}$ and $R_{0(2)}$ (pins 2 and 3, respectively) of counter 244 are coupled to an output of a NAND gate 266. Reset inputs $R_{9(1)}$ and $R_{9(2)}$ (pins 6 and 7, respectively) of counter 244 are coupled to ground as is a ground terminal (pin 10) of counter 244. The $Q_D$ output (pin 11) of counter 244 is coupled to the $Q_A$ input (pin 14) of counter 244. The $Q_A$ output (pin 12) of counter 244 is coupled to a count input (pin 1) of a divide-by-six counter 250 and to the cathode of a light-emitting diode 248. The anode of light emitting diode 248 is coupled to the source of +5 VDC through a 330 ohm resistor 248. Light-emitting diode provides a visual indication of the 1 Hz square wave produced by counter 244.

A divide-by-six counter 250 divides the 1 Hz square wave produced by counter 244 by six to produce at its $Q_D$ output (pin 8) a 1/6 Hz square wave. Illustratively, counter 250 is a SN 7492 counter manufactured by Texas Instruments configured as a divide-by-six counter. A power terminal (pin 5) of counter 250 is coupled to the source of +5 VDC (not shown) as are reset inputs $R_{0(1)}$ and $R_{0(2)}$ (pins 6 and 7, respectively) of counter 250. A ground terminal (pin 10) of counter 250 is coupled to ground.

Interval timer 42 also includes counters 254, 256 and thumbwheel switches 258, 260 which cooperate to initiate a "clear" signal when the counts accumulated in counters 254, 256 match the settings on thumbwheel switches 258, 260. Illustratively, counters 254, 256 are SN 74160 decade counters manufactured by Texas Instruments. The $Q_D$ output (pin 8) of counter 250 at which the 1/6 Hz square wave is produced is coupled to first and second inputs of a NAND gate 252, thus configuring NAND gate 252 as an inverter. An output of NAND gate 252 is coupled to clock inputs (pin 2) of counters 254, 256. Clear inputs (pin 1) of counters 254, 256 are coupled to an output of an inverter configured NAND gate 270. P enable inputs (pin 7) of counters 254, 256 are coupled to the source of +5 VDC (not shown) as are power terminals (pin 16) and load inputs (pin 9) of counters 254, 256. A T enable input (pin 10) of counter 254 is also coupled to the source of +5 VDC. A ripple carry output (pin 15) of counter 254 is coupled to a T enable input (pin 10) of counter 256 thus configuring counters 254, 256 as cascaded counters. Counters 254, 256 have BCD outputs $Q_A$, $Q_B$, $Q_C$, $Q_D$ (pins 14, 13, 12, 11, respectively) which are coupled to the cathodes of isolation diodes 259. The anodes of isolation diodes 259 are coupled to respective BCD inputs of thumbwheel switches 258, 260. A common terminal 261 of thumbwheel switch 260 and a common terminal 263 of thumbwheel switch 258 are coupled to a first input of a NAND gate 262 and through a 1k pull-up resistor 264 to the source of +5 VDC (not shown). A second input of NAND gate 262 is coupled to the output (pin 3) of timer 228. An output of NAND gate 262 is coupled to a first input of NAND gate 266. A second input of NAND gate 266 is coupled to a source of an operator initiated "Reset" signal, such as a push-button and through a 1k pull-up resistor 268 to the source of +5 VDC. An output of NAND gate 266 is coupled to first and second inputs of inverter configured NAND gate 270.

Interval timer 42 is reset back to zero and produces the "clear" signal for clearing event counter 40 when the counts accumulated in counters 254, 256 match the settings on thumbwheel switches 258, 260. When the counts accumulated in counters 254, 256 match the settings on thumbwheel switches 258, 260, the first input of NAND gate 262 to which common terminals 261, 263 of thumbwheel switches 258, 260 are coupled will be brought high. When the second input of NAND gate 262, coupled to the output (pin 3) of timer 228, goes high, i.e., when timer 228 produces its next pulse, the output of NAND gate 262 will go low. This brings the first input of NAND gate 266 to which the output of NAND gate 262 is coupled low, causing the output of NAND gate 266 to go high, producing a high going "clear" signal. This high going clear signal resets counters 244, 250 to zero and also comprises the clear signal which clocks the accumulated count in event counter 40 into storage circuit 44 and resets event counter 40 to zero. This high going clear signal is also inverted by inverter configured NAND gate 270 to produce a low going "clear" signal which resets counters 254, 256 to zero.

Referring to FIGS. 6 and 7, the operation of interval timer 42 to cause data to be transferred from event counter 40 to storage circuit 44 and to clear event counter 40 is described. The output of NAND gate 266 is coupled to the negative-transition input (pin 3) of one-shot 272 and to the negative-transition input (pin 3) of one-shot 274. The output of NAND gate 266 is also coupled to enable inputs of storage modules 281, 283, 285. When NAND gate 266 produces the high going clear signal, it causes the data in counters 280, 282, 284, to be transferred into storage modules 281, 283, 285, which retain this data when the clear signal falls low again. The data in storage modules 281, 283, 285, which represent the accumulated count of event counter 40 at the end of the measuring interval, sets the data outputs of storage modules 281, 283, 285. The data outputs of storage modules 281, 283, 285 drive display modules 293, 295, 297, respectively, so that display modules 293, 295, 297 display the counts which had been accumulated by counters 280, 282, 284, respectively, at the end of the measuring period. Thus, visual display 47 will display the total number of feeding events detected by ultrasonic insect detector 10 at the end of the measuring period.

One-shot 274 de-glitches the clear signal produced at the output of NAND gate 266 of interval timer 42 and also inverts it to produce a low going "clear" signal. This low going clear signal produced at the output (pin 1) of one-shot 274 resets counters 280, 282, 284 of event counter 40 back to zero. During this clear sequence, the presence of the high going clear signal at the negative-transition input (pin 3) of one-shot 272 disables one-shot 272 from producing a count pulse in response to a count pulse from Schmitt trigger 38. Once the clear sequence is over and the output of NAND gate 266 of interval timer 42 has gone low again, one-shot 272 will no longer be disabled and will again produce count pulses in response to count pulses from Schmitt trigger 38.

Although the invention has been described in detail with reference to a certain preferred embodiment, variations and modifications exist within the scope and spirit of the invention as described and defined in the following claims.

What is claimed is:

1. An apparatus for detecting insects, comprising means for detecting ultrasonic signals generated by the tearing of material by insects as they feed on the material and producing first electrical signals therefrom, means for processing the first electrical signals to generate second electrical signals indicative of the feeding activity of the feeding insects, and means for coupling the ultrasonic signal detecting means to the processing means.

2. The apparatus of claim 1, and further including a comparator to produce a digital pulse from each second electrical signal having a magnitude above a threshold level and means for coupling an input of the comparator to an output of said processing means.

3. The apparatus of claim 1, wherein the feeding of the insects on materials causes the tearing of the material and produces mechanical disturbances which generate the ultrasonic signals, and the means for processing the first electrical signals to generate the second electrical signals includes means for generating the second electrical signals from the first electrical signals having a magnitude above a selected level, the apparatus further including means responsive to the second electrical signals for indicating the feeding activity of the insects, and means for coupling the indicating means to the processing means.

4. The apparatus of claim 3, wherein the ultrasonic signal detecting means comprises an ultrasonic transducer.

5. The apparatus of claim 3, wherein the processing means includes means for setting the selected level.

6. The apparatus of claim 3, wherein the indicating means includes an audio amplifier coupled to the output of the processing means, and an audio transducer coupled to the output of the audio amplifier to provide an audio indication of insect feeding activity.

7. The apparatus of claim 3, wherein the indicating means includes counting means for summing the number of second electrical signals generated during a predetermined time period, each second electrical signals indicative of an individual insect feeding event, the counting means driving a visual display to display the number of insect feeding events summed.

8. The apparatus of claim 1 wherein each detected ultrasonic signal is an oscillatory signal generated by a mechanical disturbance in a material on which an insect is feeding caused by the insect taking a bite out of the material, and the means for producing the first electrical signals from the detected ultrasonic signals produces an oscillating first electrical signal from each detected ultrasonic signal, the means for generating the second electrical signals including an envelope detector for producing the second electrical signals by producing envelopes of the first electrical signals.

9. The apparatus of claim 8 and further including means for comparing the second electrical signals to a threshold level and producing a digital pulse each time a second electrical signal has a magnitude above the threshold level and means for coupling the comparing means to the envelope detector.

10. The apparatus of claim 9 wherein the envelope detector comprises a full wave rectifier for full wave rectifying the first electrical signals and an averaging filter coupled to an output of the full wave rectifier.

11. The apparatus of claim 9 wherein the comparing means includes means for producing the digital pulses in a form suitable for input to a computer.

12. The apparatus of claim 9 and further including means for counting the digital pulses, means for displaying count accumulated by the counting means, and means for coupling the displaying means to the counting means.

13. The apparatus of claim 12 and further including means for timing a measuring period, means for storing the count accumulated in the counting means at the end of the measuring period, means for coupling the storing means to the counting means, means for coupling the storing means to the timing means, second display means for displaying the count stored in the storing means, and means for coupling the second display means to the storing means.

14. The apparatus of claim 13 wherein the timing means includes means for repetitively timing measuring periods, the storing means including means for replacing the count stored in it with the count accumulated by the counting means at the end of each measuring period, the counting means including means responsive to the timing means for resetting itself to zero at the end of each measuring period, and means for coupling the counting means to the timing means.

15. The apparatus of claim 8 and further including means for producing audible signals indicative of the insect feeding activity from the second electrical signals.

16. The apparatus of claim 15 wherein the audible signal producing means includes an audio amplifier, a speaker coupled to an output of the audio amplifier, and means for coupling the audio amplifier to an output of said envelope detector.

17. The apparatus of claim 16 wherein the envelope detector includes a full wave rectifier for full wave rectifying the first electrical signals and an averaging filter coupled to an output of the full wave rectifier.

18. The apparatus of claim 17 wherein the averaging filter comprises a low-pass filter having a cut-off frequency of 5 kHz.

19. An ultrasonic insect detector for detecting insects by detecting feeding events, a feeding event being a mechanical disturbance in a material on which insects are feeding caused by an insect tearing the material as it takes a bite of the material, each feeding event producing an ultrasonic signal, the system comprising
   an ultrasonic transducer sensitive only to frequencies within a narrow frequency range for detecting the ultrasonic signals and generating first electrical signals therefrom,
   a preamplifier,
   means for coupling an input of the preamplifier to the ultrasonic transducer,
   a band-pass filter to pass only the narrow range of frequencies to which the ultrasonic transducer is sensitive,
   means for coupling an output of the preamplifier to an input of the band-pass filter,
   an envelope detector for producing envelopes of the preamplified and band-pass filtered first electrical signals wherein each envelope is indicative of a feeding event, and
   means for coupling an output of the band-pass filter to an input of the envelope detector.

20. The system of claim 19, wherein the envelope detector includes a full wave rectifier and an averaging filter coupled to an output of the full wave rectifier.

21. The system of claim 19, and further including means responsive to the envelopes produced by the envelope detector for providing an audio output corresponding to the degree of insect feeding activity.

22. The system of claim 21, wherein the audio output means includes an audio amplifier coupled to an output of the envelope detector and an audio transducer coupled to an output of the audio amplifier.

23. The system of claim 19, and further including digital output means for generating an output signal corresponding to a logical one when an envelope produced by the envelope detector is above a predetermined threshold and a logical zero when the envelope is below the predetermined threshold.

24. The system of claim 23, wherein the digital output means includes a comparator for generating the output signal corresponding to a logical one when the envelope from the envelope detector is above the predetermined threshold and a logical zero when the envelope from the envelope detector is below the predetermined threshold, a digital counter for counting the output signals produced by the comparator which are logical ones and for driving a visual display for displaying a number which represents the number of insect feeding events counted, and means for coupling an output of the comparator to an input of the digital counter.

25. A method of detecting insects comprising detecting ultrasonic signals produced by mechanical disturbances in material on which the insects are feeding, the mechanical disturbances being caused by the tearing of the material on which the insects are feeding.

26. The method of claim 25 and further including the step of producing electrical signals indicative of the feeding activity of the insects from the detected ultrasonic signals.

27. The method of claim 26 wherein the ultrasonic signals produced by the mechanical disturbances are oscillatory and the step of producing electrical signals indicative of the feeding activity of the insects includes the steps of detecting the envelopes of the ultrasonic signals and producing envelope signals of each detected ultrasonic signals wherein each envelope signal is indicative of a mechanical disturbance in the material on which the insects are feeding caused by an insect taking a bite of the material.

28. The method of claim 27 and further including the step of producing digital pulses from the envelope signals wherein each digital pulse represents a bite taken from the material by an insect by comparing each envelope signal to a threshold and producing a digital pulse when the envelope signal has a magnitude which exceeds the threshold.

29. The method of claim 28 and further including the step of counting the digital pulses and displaying the count.

30. The method of claim 29 and further including the steps of storing the counted digital pulses after a measuring interval and displaying the stored counted pulses.

31. The method of claim 28 and further including the step of producing audio signals indicative of the feeding activity of the insects by amplifying the envelope signals and broadcasting the amplified envelope signals over a speaker.

32. A method of detecting insects by detecting feeding events wherein a feeding event is a mechanical disturbance created in material on which an insect is feeding caused by an insect taking a bite of the material, comprising the steps of detecting ultrasonic signals produced by the mechanical disturbances wherein each detected ultrasonic signal is indicative of a feeding event and is an oscillatory signal, producing electrical signals from the detected ultrasonic signals, detecting the envelopes of the electrical signals and producing an envelope signal for each electrical signal which exceeds a set threshold, and providing an indication of the feeding activity of the insects based upon the envelope signals.

33. The method of claim 32 and further including the step of setting the set threshold to distinguish between relatively lower level detected ultrasonic signals and relatively higher level detected ultrasonic signals.

34. The method of claim 32 wherein the step of providing an indication of the feeding activity of the insects based upon the envelope signals includes the steps of comparing the envelope signals to a second threshold and producing a digital pulse for each envelope signal which exceeds the second threshold.

35. The method of claim 34 wherein the step of providing an indication of the feeding activity of the insects based upon the envelope signals includes the steps of counting the digital pulses and displaying the accumulated count.

36. The method of claim 32 wherein the step of providing an indication of the feeding activity of the insects based upon the envelope signals includes the step of transducing the envelope signals to audible signals.

* * * * *

UNITED STATES PATENT AND TRADEMARK OFFICE
CERTIFICATE OF CORRECTION

PATENT NO. : 4,809,554

DATED : March 7, 1989

INVENTOR(S) : Richard E. Shade et al.

It is certified that error appears in the above-identified patent and that said Letters Patent is hereby corrected as shown below:

At column 5, line 59, please delete "0.47 µF" and insert therefor --.047 µF--.

Signed and Sealed this

Twenty-ninth Day of August, 1989

Attest:

DONALD J. QUIGG

*Attesting Officer*     *Commissioner of Patents and Trademarks*